United States Patent [19]

McDermott

[11] 4,244,878

[45] Jan. 13, 1981

[54] PREPARATION OF MALEIC ANHYDRIDE

[75] Inventor: Joseph X. McDermott, River Edge, N.J.

[73] Assignee: Halcon Research and Development Corporation, New York, N.Y.

[21] Appl. No.: 931,631

[22] Filed: Aug. 4, 1978

Related U.S. Application Data

[62] Division of Ser. No. 822,290, Aug. 5, 1977, Pat. No. 4,151,116.

[51] Int. Cl.³ .......................................... C07D 307/60
[52] U.S. Cl. ............................................... 260/346.75
[58] Field of Search ................................... 260/346.75

[56] References Cited

U.S. PATENT DOCUMENTS 3,888,886  6/1975  Young et al. ................... 260/346.75

FOREIGN PATENT DOCUMENTS 1460971  1/1977  United Kingdom .

Primary Examiner—Henry R. Jiles
Assistant Examiner—Bernard Dentz
Attorney, Agent, or Firm—William C. Long; David Dick; Riggs T. Stewart

[57] ABSTRACT

A catalyst for the oxidation of butane to produce maleic anhydride comprising a substrate containing phosphorus and vanadium, and optionally also containing an activator, is characterized by the presence of at least one post-deposited promoter.

9 Claims, No Drawings

PREPARATION OF MALEIC ANHYDRIDE

This is a division of application Ser. No. 822,290 filed Aug. 5, 1977 now U.S. Pat. No. 4,151,116.

This invention relates to the preparation of maleic anhydride by the catalytic molecular oxygen oxidation of butane and is more particularly concerned with an improved catalyst for use in carrying out that oxidation.

Maleic anhydride is of significant commercial interest throughout the world, and is extensively used in the manufacture of alkyd resins. It is also a versatile intermediate for chemical syntheses. Consequently, large quantities of maleic anhydride are produced each year to satisfy these needs. The production of maleic anhydride by the catalytic oxidation of benzene and butene is well known and the principal method currently employed for manufacturing maleic anhydride is by the air oxidation of benzene in the presence of certain heavy metal oxide catalysts. Comparatively little attention has been given to the use of saturated aliphatic hydrocarbons, e.g. butane, as feedstocks for the preparation of maleic anhydride. This is due, in part at least, to the fact that butane is more difficult to oxidize than benzene or butene, often resulting in low conversions to maleic anhydride. Although catalysts for the oxidation of saturated aliphatic hydrocarbons such as butane are known, the yields of the desired maleic anhydride product over the known catalyst are, in most cases, insufficiently high to make such butane competitive with benzene as a feedstock.

In general, catalysts proposed for the oxidation of butane to maleic anhydride have been based upon vanadium and phosphorus. Thus, the use of a vanadium-phosphorus complex catalyst to oxidize butane to maleic anhydride is described in Bergman et al, U.S. Pat. No. 3,293,268. This catalyst, however, requires an operating temperature greater than 500° C. and, in general, reported yields are relatively low and not commercially attractive. In order to improve the effectiveness of vanadium-phosphorus catalysts, it has been proposed to incorporate various additives, frequently referred to as "activators", "stabilizers", "promoters", and the like. For example, Freerks et al U.S. Pat. No. 3,832,359 proposes the addition of iron to phosphorus and vanadium, and Raffelson U.S. Pat. No. 3,867,411 further modifies the iron-modified phosphorus vanadium catalyst by the addition of chromium. Boghosian U.S. Pat. No. 3,862,146 adds to phosphorus and vanadium a catalyst activator which is zinc, bismuth, copper or lithium. In British Pat. No. 1,475,309, it is proposed to increase the effectiveness of a phosphorus-vanadium catalyst by adding an activator which is cobalt or nickel. British Pat. No. 1,460,971 is concerned with a catalyst in which the added component is titanium, zirconium, hafnium or silicon. More recently, Young et al U.S. Pat. No. 3,888,886 discloses phosphorus-vanadium catalysts modified with various transition metals having varying effectiveness, the more active being chromium, iron, hafnium, zirconium, cerium and lanthanum. Although other metals are disclosed, they are characterized as having little or no activity. These metals include manganese, zinc, ruthenium, molybdenum, tin, titanium, antimony, thorium and praseodymium.

While these various additives do bring about some improvement in the phosphorus-vanadium catalyst suitable for oxidizing butane to maleic anhydride, there remains much room for improvement, particularly from the standpoint of high conversions and yields.

It is accordingly an object of this invention to provide an improved catalyst based upon phosphorus and vanadium.

It is a further object of the invention to provide a catalyst of the character indicated which is of particular effectiveness in the oxidation of butane to maleic anhydride.

It is a still further object of the invention to provide a promoted phosphorus-vanadium catalyst which makes possible improved yields and high conversions in the oxidation of butane to maleic anhydride.

Another object of the invention is to provide a process for the catalytic oxidation of butane to maleic anhydride with improved yields and improved selectivities.

These and other objectives are realized in accordance with the present invention by a catalyst comprising a substrate containing phosphorus and vanadium, and optionally containing a promoting or activating additive, and a promoter deposited upon the substrate after the substrate has been formed, i.e. a "post-deposited" promoter. More particularly, the catalyst of this invention comprises a pre-formed substrate containing phosphorus and vanadium, and a post-deposited promoter which is typically magnesium, calcium, scandium, yttrium, lanthanum, uranium, cerium, chromium, manganese, iron, cobalt, nickel, copper, zinc, aluminum, gallium, indium, silicon, germanium, tin, bismuth, antimony or tellurium. When an additive or activator is incorporated in the substrate, it is typically titanium, zinc, hafnium, lithium, magnesium, calcium, iron, cobalt, nickel, copper, tin, bismuth, uranium, the rare earth metals (particularly cerium and lanthanum), chromium, cadmium or aluminum.

The term "substrate" is used to designate a catalyst composition which has been prepared in any convenient manner, e.g. by any of the processes well known to the art, and has been dried and activated and can, in itself, serve as a catalyst in the oxidation of butane to produce maleic anhydride. This preformed catalytically active substrate is, however, in accordance with the invention, treated so that it is significantly more effective as a catalyst by having a promoter applied to its surface, e.g. by treating it with a solution or dispersion containing the promoting element, so that the substrate is post-coated or post-impregnated with the promoting element. In accordance with the invention, one or more of the promoting elements may be post-deposited upon the substrate, and this post-deposition may take place in one or more treating steps, e.g. one of the promoting elements may be applied in a first step, and the other of the promoting elements may be applied in a second step. As will be apparent from the above listing of typical additives and typical promoters, the catalyst of the invention may contain the same element as an integral component of the substrate and serving as an activating additive, hereinafter referred to simply as an "activator", and also as a post-deposited promoter. Usually, however, the activator integrally incorporated in the substrate and the post-deposited or "surface" promoter are different.

Best results are obtained in accordance with the invention when the phosphorus and vanadium are present in the substrate in the atomic ratio of 0.9:1 to 0.5:1, preferably 1:1 to 1.3:1, although other ratios may be employed. Generally, the ratio of phosphorus to vanadium is at least 1 to 1, and not more than 1.25 to 1. The amount of the integrally incorporated activator in the substrate, expressed as an atomic ratio in relation to V, is variable over a wide range, but generally it lies in the range of 0.01 to 0.3 atom per atom of vanadium in the substrate. Preferably, however, the amount of activator is 0.01 to 0.15 atom per atom of vanadium, and most preferably, 0.03 to 0.08 atom per V atom.

Similarly, the amount of post-deposited promoter may vary over a large range, but preferably it is at least 0.001 atom per atom of vanadium in the substrate. Typically, the amount of promoter will lie within the range of 0.001–0.2 atom per atom of vanadium, and preferably the amount will be in the range of 0.01–0.06 atom per V atom.

When the atomic amount of vanadium in the substrate is taken as 1, the amount of integrally-incorporated activator will typically be 0.01 to 0.3, preferably 0.01 to 0.15, and most preferably 0.03 to 0.08, whereas the amount of post-deposited promoter will typically be 0.001 to 0.2, preferably 0.01 to 0.06.

The catalyst of this invention can be prepared in any convenient manner, e.g. using techniques already known by persons skilled in the art. The following procedures, however, have been found to be particularly suitable and to yield catalysts of favorable activity. It will be understood, however, that the invention is not limited to catalyst prepared by these particular methods of preparation. Thus, the substrate of the catalyst is preferably prepared by forming a solution of a vanadium compound, a phosphorus compound, and if used, a compound of the activator metal in an appropriate solvent, concentrated hydrochloric acid being particularly suitable as a solvent for the substrate components.

If the substrate is to be used in non-supported form, e.g. in the form of a pellet or other shape, the solution is evaporated to dryness and the resulting finely divided particles are pelletized or formed into other shapes in conventional manner.

On the other hand, if the substrate is to be in supported form, the aqueous acidic solution is deposited upon a support or carrier and dried. The drying of the solution by evaporation of its aqueous content is readily effected merely by heating it in air or in an inert atmosphere, e.g. in nitrogen at 90° to 200° C., typically about 100° C. until dried. Thereafter, the dried composition, either in supported form or as a powder, or after forming, is activated by calcination, preferably in air, at a temperature of at least about 300° C. Preferably, the catalyst is activated before forming. Alternatively, activation can be accomplished with oxygen or in an inert atmosphere, e.g. with nitrogen, argon, or other inert gas.

The phosphorus, vanadium and optional activator components of the substrate can be incorporated in any convenient form, depending upon the particular solvent being used to place them in solution, as will be well understood by persons skilled in the art. While hydrochloric acid, e.g. in concentrated form or in constant boiling form, is the preferred solvent, other solvents can be readily used, depending upon the form of the compound being employed. For example, polar organic solvents such as alcohols, amides, e.g. formamide, and the like can be used.

Thus, suitable phosphorus compounds include phosphoric acids, such as metaphosphoric acid, orthophosphoric acid, triphosphoric acid and pyrophosphoric acid; phosphorus oxides, such as phosphorus pentoxide; phosphorus halides and oxyhalides, such as phosphorus oxyiodide, phosphorus pentachloride and phosphorus oxybromide; phosphorus salts such as mono-, di- and tri-ammonium phosphates, and organophosphorus compounds such as ethyl phosphate and methyl phosphate. However, phosphoric acids, such as orthophosphoric acid, and phosphorus pentoxide are preferred.

Representative of vanadium compounds which can be employed are vanadium oxides, such as vanadium pentoxide and vanadium trioxide; vanadium halides and oxyhalides, such as vanadium trichloride, vanadium tribromide, vanadyl chloride, vanadyl trichloride, vanadyl dichloride, vanadyl bromide, vanadyl dibromide and vanadyl tribromide; vanadium-containing acids such as metavanadic acid and pyrovanadic acid; and vanadium salts, both organic and inorganic, such as ammonium metavanadate, vanadium sulfate, vanadium phosphate, vanadyl formate, vanadyl acetoacetonate and vanadyl oxalate. Vanadium pentoxide is, however, preferred.

Similarly, a wide variety of compounds can be employed to introduce the activator element into the substrate. These activator compounds, however, should be at least partially soluble in the solvent medium used in the particular preparation in order to be best suited for combination with the phosphorus and vanadium components of the substrate. Typical compounds of titanium, which is the preferred activator, include titanium halides, such as titanium dichloride, titanium trichloride, titanium tetrachloride, titanium dibromide, titanium tribromide, titanium tetrabromide, titanium diiodide, titanium triiodide, titanium tetraiodide, and titanium tetrafluoride; titanium salts such as titanium phosphates and titanium sulfates; and organic titanium compounds, e.g. alkyl titanates such as methyl titanate, ethyl titanate, isopropyl titanate and butyl titanate; and aryl titanates such as phenoxy titanium trichloride and phenyl titanate.

Corresponding compounds of the other activators are suitably used, the above-specified compounds of titanium merely being illustrative of the forms in which all of the activator elements may be incorporated.

When two activators are to be incorporated, it is, of course, possible to combine them in one compound, and similarly, the titanium compound may include another metal which has no apparent effect upon the catalytic activity of the substrate. Typical of such compounds are potassium fluorotitanate, inorganic titanates such as alkali metal titanates, alkaline earth metal titanates, aluminum titanate and lead titanate. In like manner, the activator metal may be included in the compound supplying the phosphorus or vanadium component of the substrate, e.g. iron or zinc or copper phosphate. It is preferred, however, that each component be added in the form of a compound which does not introduce another metal into the composition.

The promoters to be post-deposited upon the substrate in accordance with this invention are preferably applied to the substrate in a form which does not attack the substrate. Water, for example, does tend to have an adverse action and it is preferred, therefore, to employ an organic solvent. Any organic solvent such as an ether, e.g. dibutyl ether or tetrahydrofuran, an alcohol, e.g. isopropyl alcohol, a ketone, e.g. methylethyl ketone, a carboxylic acid, e.g. acetic acid, a nitrogen-containing compound, e.g. formamide and ethylene diamine, and the like can be used. The invention is thus in no way limited to the use of any particular solvent, but tetrahydrofuran and formamide are preferred. The promoter should, therefore, be in a form which is at least partially soluble in the solvent to be used. Typically, the promoter will be in the form of a salt, e.g. an inorganic salt such as chloride, bromide or iodide, or an organic salt such as a formate or acetate. When, for example, zinc is to be used as the promoter, it is preferably used in the form of zinc chloride, zinc bromide, zinc iodide, zinc formate or zinc acetate. When any of the other promoter metals are to be post-deposited upon the substrate, they are also preferably used in the form of the above-recited salts. It has also been found that the addition of a small amount of a phosphoric acid, e.g. orthophosphoric acid, or a boric acid, e.g. ortho boric acid, has a favorable effect upon the activity of the promoter. The amount of phosphoric or boric acid is typically 0.01 to 0.10 mol per mol (expressed as P or B) based on the V in the substrate, or expressed another way, 0.3 to 3 atoms per atom of promoter metal in the promoter solution.

As previously mentioned, the substrate is formed by combining the phosphorus component, the vanadium component and, if used, the activator component in a solution and then evaporating the solution to dryness to form a dry particulate mass or, if the substrate is to be supported, the solution is applied to the support or carrier particles and thereafter evaporated to dryness to provide support or carrier particles coated or impregnated with the catalytic components of the substrate. Although it is not essential from the standpoint of the invention, it is desirable that a substantial portion, e.g. at least about 50% of the vanadium be in the tetravalent form. As a result of having been in solution in concentrated hydrochloric acid, the vanadium will ordinarily be mostly in the tetravalent state. The same is true when another acid with reducing properties, such as oxalic acid, is the acidifying agent in the aqueous solution, instead of hydrochloric acid or other hydrohalic acid. While concentrated acidic solutions are preferred, more dilute solutions may also be used. Unacidified water can be used as the solvent, and in this case, it is preferable to include in the solution an organic reducing agent such as an aldehyde or an amine.

Following the drying of the solution containing the substrate components, the dried particulate mass is preferably formed into a shape suitable for use in a butane oxidation reactor, e.g. the particles can be pelletized or prilled or tabletted or otherwise formed into structures. As previously mentioned, the particles are preferably activated, as described below, before they are shaped. Methods for shaping catalyst particles are well known in the art and form no part of the present invention. Typically, the particles to be shaped are wetted with enough water to form viscous putty, and there are suitably added a lubricant such as stearic acid and a binder such as polyvinyl alcohol. The moist viscous mass is then shaped by extrusion or pelletting, or otherwise, in conventional manner as will be obvious to persons skilled in the art.

When the substrate is to be supported on a carrier, any of the carriers known in the art may be employed, including silica gel, silica alumina, silica, kieselguhr, alundum, fuller's earth, pumice, silicon carbide, asbestos, and the like, the carrier suitably being inert to the solution containing the substrate components, which is applied to the carrier and resistant to the conditions encountered in the catalytic oxidation of butane. The carrier or support preferably has a low surface area, e.g. from about 0.01 to 10 square meters per gram. The amount of substrate components deposited on the carrier should be sufficient substantially to coat the surface of the carrier. For use in a fixed-bed reactor installation, the size of the coated or impregnated carrier will preferably be from about 2½ to about 10 mesh. The carriers may be of a variety of shapes, the preferred shape being cylindrical or spherical. The size of the catalyst particles used in fluidized bed reactors is quite small, however, usually varying from about 10 to about 150 microns, and in such systems the substrate normally will not be provided with a carrier but will be formed into the desired particle size after drying from solution. The carrier is coated by spraying the substrate solution upon it or by tumbling it in the solution while heating it to evaporate the water.

The dried substrate, whether in its initial particulate form which may be first subdivided, e.g. for use in a fluid-bed reactor or in its shaped form, e.g. as pellets, or in supported form, is then "activated" in the manner previously mentioned by heating it at an elevated temperature, e.g. at least about 300° C. in the presence of oxygen suitably in the form of air on in an inert atmosphere, preferably for a period of 30 to 300 minutes. If the activation is effected in an air or oxygen atmosphere, care should be taken to keep the temperature below 500° C. in order to avoid undue oxidation of tetravalent vanadium to pentavalent vanadium in order that an appreciable portion of the vanadium in the activated substrate will still be present in the tetravalent form.

In accordance with the invention, the activated substrate is now coated or impregnated with the desired promoter. The procedure for applying the promoter to the substrate is in no way critical and procedures such as used in coating a carrier may be used. Typically, the promoter solution may be used in a volume equal to the void space of the substrate and, when added to the substrate, the solution may be imbibed by the substrate pores. Alternatively, the substrate may be immersed in an excess volume of promoter solution, then removed and allowed to drain. The concentration of promoter in the solution is selected so that the desired quantity of promoter is retained by the catalyst. In a third method, the promoter solution is sprayed upon the particles or shapes of substrate, which are tumbled to achieve uniformity. The thus-treated substrate is then dried and activated in the manner described above in connection with making a supported substrate. If desired, activation can be effected in the reactor in which the catalyst composition of the invention is to be employed, i.e. by so-called in situ activation. In this case, the catalyst is charged to the reactor and a butane-air mixture is passed through it at temperatures of 350° to 450° C. for 2 to 12 hours.

Butane is oxidized in the presence of the above-described catalyst of this invention in any conventional manner, and the catalyst is useful in both fluid-bed reactors and in fixed-tube reactors and the conditions of operation of such reactors are well known to persons skilled in the art. Typically, the oxidation of butane to maleic anhydride is carried out by means of air or other molecular oxygen-containing gases such as mixtures of carbon dioxide and oxygen or mixtures of nitrogen or steam with air or oxygen. Air is preferred. The oxidation is carried out at temperatures of 350° to 500° C., preferably 400°–475° C. Preferably the concentration of butane in the feed will be 1.0 to 1.6 volume % with $O_2$ above 10 volume %, and 1.5 to 5% with $O_2$ below 0.10 volume %, and space velocities of 1000 to 4000 $hr^{-1}$ are preferably employed in fixed-bed reactions and 500 to 2000 $hr^{-1}$ in fluidized-bed operations. The reaction may be carried out at atmospheric, sub-atmospheric or super-atmospheric pressure, but substantially atmospheric pressure is preferred. Typically, the reaction pressure is about 1 to 7 atmospheres absolute. As previously mentioned, the reaction can be carried out in any reactor suitable for effecting vapor-phase oxidation reactions, but preferably the fixed catalyst bed is employed. The catalyst-containing tubes of such reactors can vary in diameter from, for example 0.25 inch to 1.5 inches and the length can vary from, for example, 6 inches to 10 feet or more. It is desirable to have the surfaces of the reactors at relatively constant temperature, and some medium to conduct heat from the reactors is desirable to aid temperature control. Such media include Woods metal, molten sulfur, mercury, molten lead and eutectic salt baths. A metal block reactor whereby the metals surrounding the tube act as a temperature regulating body can also be used. The reactor or reaction tubes can be formed from any convenient material, typically stainless steel or carbon steel.

Maleic anhydride prepared by using the catalyst of this invention can be recovered by any number of means well known to those skilled in the art. For example, the maleic anhydride can be recovered by direct condensation, or by absorption in suitable media, e.g. water with subsequent separation, dehydration and purification.

The following examples will serve to provide a fuller understanding of the invention, but it is to be understood that these examples are given for illustrative purposes only, and are not to be interpreted as limiting the invention in any way. In the examples, the terms "conversion", "selectivity" and "yield" have their conventional meanings in this art, viz $$\text{Conversion (\%)} = \frac{\text{mols butane reacted}}{\text{mols butane fed}} \times 100$$

$$\text{Selectivity (\%)} = \frac{\text{mols maleic anhydride produced}}{\text{mols butane reacted}} \times 100$$

$$\text{Yield (\%)} = \frac{\text{grams maleic anhydride produced}}{\text{grams butane fed}} \times 100$$

EXAMPLE I

A substrate containing phosphorus and vanadium is prepared by refluxing 500 grams of $V_2O_5$ in 6500 cc of concentrated hydrochloric acid until the $V_2O_5$ dissolves and the vanadium is now apparently predominantly in the form of $VOCl_2$. Then 730 grams of 85% phosphoric acid is added and the resulting mixture refluxed in 4 hours. The final solution is then evaporated to dryness by heating in a glass vessel for approximately 5 hours at up to 200° C. The resulting dry solid is activated by heating it to 400° C. for four hours in a furnace in the presence of a continuous stream of air. The resulting powder is then formed into granules of approximately 14–18 mesh size by mixing the powder with a 4% aqueous polyvinyl alcohol solution and shaping, drying it at 110° C. and reactivating by heating at 400° C. for 2 hours in the presence of air. The substrate thus produced has a P/V atomic ratio of 1.15:1. This product is designated as substrate A.

EXAMPLE II

Example I is repeated except that 41 grams of titanium tetrachloride is added to the solution obtained by refluxing the $V_2O_5$ prior to addition of the phosphoric acid. The resulting substrate has a P/V/Ti atomic ratio of 1.15:1:0.04 and is designated as substrate B. Example I is again repeated except that 62 grams of titanium tetrachloride is added. The resulting substrate has a P/V/Ti atomic ratio of 1.15:1:0.06 and is designated as substrate C.

EXAMPLE III

Substrate A is then treated to deposit zinc upon its surface in accordance with this invention by adding a solution of zinc chloride in formamide (10 ml) to 50 grams of the substrate A granules. The solution volume is just sufficient to fill the internal porosity of the granules and the thus-treated granules are then heated to 400° C. for 2 hours in a continuous stream of air to activate them. In this manner there are prepared three catalysts containing post-deposited zinc in the atomic ratios, per atom of V in the substrate, of 0.01, 0.03 to 0.12.

EXAMPLE IV

Example III is repeated except that instead of the zinc chloride solution, there is used in one case 0.8 cc of 85% phosphoric acid, and in another case, 8.6 grams phosphomolybdic acid in 10 cc of formamide. There are thus produced two catalysts, one of which contains post-deposited phosphorus in the atomic ratio of 0.05 per atom of V in the substrate, and the other of which contains post-deposited phosphorus and molybdenum in the atomic ratio of 0.01 P and 0.12 Mo per atom of V in the substrate.

EXAMPLE V

Example III is repeated except that substrate B is used and the amount of zinc chloride used is such that the resulting catalyst contains post-deposited zinc in the atomic proportion of 0.04 per atom of V in the substrate.

EXAMPLE VI

Following the procedures of Examples III and IV but using substrate C, there are produced a series of catalysts containing various metals in various quantities post-deposited upon the substrate, some in combination with phosphorus and, in one case, in combination with boron, which is added in the form of a formamide solution of boric acid. The identity and amounts of the promoters are tabulated in Table 1.

EXAMPLE VII

Substrates A and B as well as the several catalysts comprising substrates A and B with post-deposited promoters prepared in Examples III, IV and V are evaluated for their activity in the oxidation of butane. For these evaluations there is used a ⅜" U-tube reactor immersed in a salt bath. In each case the charge or bed of the catalyst to be tested is 50 ml (approximately 40 g.) and the reaction is carried out at atmospheric pressure. A mixture of 1.5 volume % of n-butane in air is passed over the catalyst bed at a space velocity of 1200 $hr^{-1}$. The salt bath temperature is held at approximately 450° C. for about eight hours to achieve additional activation, and selectivity and conversion to maleic anhydride are then determined over the range of 380° C. to 500° C. The results of these conversions are set forth in Table 1 below. In this table the first column identifies the substrate, and the second column identifies the post-deposited promoters and indicates the atomic quantity of the promoter per atom of V in the substrate. The third column shows the temperature in °C. at which 80 mol % conversion of butane is achieved. The fourth column shows the mol % selectivity to maleic anhydride at 80 mol % conversion and the last column lists the maximum weight percent yield of maleic anhydride.

TABLE 1

| Substrate | Promoters | | $T_{80}$ | $S_{80}$ | Maleic Anhydride Yield |
|---|---|---|---|---|---|
| A | none | | 500 | 47 | 65 |
| B | none | | 470 | 47 | 68 |
| C | none | | 460 | 47 | 68 |
| A | .01 Zn | | 455 | 53 | 76 |
| A | .03 Zn | | 455 | 55 | 77 |
| A | .12 Zn | | 450 | 53 | 73 |
| A | .05 P | | 485 | 48 | 70 |
| A | .12 P—Mo | | 480 | 40 | 50 |
| B | .04 Zn | | 460 | 53 | 76 |
| C | .04 Li | .05 P | 455 | 47 | 65 |
| C | .04 Na | .05 P | 460 | 48 | 72 |
| C | .04 Mg | | 420 | 47 | 68 |
| C | .04 Mg | .05 P | 415 | 58 | 83 |
| C | .03 Al | | 410 | 55 | 80 |
| C | .04 Al | | 405 | 58 | 85 |
| C | .06 Al | | 430 | 43 | 60 |
| C | .04 Al | .05 P | 435 | 53 | 76 |
| C | .04 Ca | .05 P | 415 | 56 | 80 |
| C | .04 Cr | | 410 | 54 | 80 |
| C | .04 Mn | | 410 | 52 | 80 |
| C | .04 Fe | | 410 | 53 | 80 |
| C | .04 Co | | 410 | 48 | 70 |
| C | .04 Ni | | 410 | 52 | 75 |
| C | .04 Cu | | 425 | 50 | 70 |
| C | .04 Zn | | 420 | 58 | 84 |
| C | .03 Zn | .05 P | 420 | 62 | 88 |
| C | .04 Zn | .05 B | 415 | 55 | 82 |
| C | .03 Ga | | 420 | 53 | 78 |
| C | .04 Ge | .05 P | 420 | 56 | 82 |
| C | .04 Cd | .05 P | 450 | 45 | 70 |
| C | .04 In | .05 P | 415 | 60 | 86 |
| C | .04 Sn | .05 P | 420 | 53 | 76 |
| C | .03 La | .05 P | 415 | 56 | 80 |
| C | .04 U | | 425 | 48 | 68 |
| C | .04 Ce | | 430 | 61 | 87 |
| C | .04 Te | | 415 | 55 | 81 |
| C | .04 Sb | | 430 | 55 | 80 |
| C | .03 Bi | | 440 | 48 | 72 |
| C | .03 Ga | .02 Sb | 415 | 57 | 85 |
| C | .04 Zn | .02 Sb | 415 | 61 | 92 |
| C | .03 Si | | 430 | 53 | 75 |
| C | .03 Sc | | 420 | 52 | 77 |
| C | .03 Y | | 420 | 52 | 77 |

EXAMPLE VIII

In order to compare the effect of a substrate having a surface-deposited promoter metal in accordance with the invention against a substrate having the same metal integrally incorporated in the substrate, several of the promoter metals listed in Table 1 are incorporated in the making of a substrate to provide substrates corresponding to substrates A and C, but, in addition, containing the integrally-incorporated metal. Thus, Example 1 is repeated several times and, in each case, there is incorporated in the solution a soluble salt respectively of magnesium, cadmium, manganese, iron, lanthanum, zinc and aluminum in an amount to provide an atomic ratio of 0.2 per atom of V. In like manner, Example II is repeated several times, and in each case, there is incorporated in the solution a soluble salt, respectively, of cadmium, tin, zinc and copper. In the case of tin and copper, the amounts of these metals used is in the atomic ratio of 0.04 per atom of V, corresponding to the amount of titanium in the substrate. In the case of cadmium and tin, these elements are used in the atomic ratio of 0.08 per atom of V, and the amount of titanium is also 0.08 per atom of V. Table 2 below lists the several catalyst compositions made as described above and shows the results of the tests for activity in oxidizing butane to maleic anhydride carried out in the manner described in Example VII.

TABLE 2

| Catalyst | $T_{80}$ | $S_{80}$ | Maleic Anhydride Yield |
|---|---|---|---|
| P/V/Mg | 470 | 20 | 30 |
| P/V/Cd | 480 | 40 | 60 |
| P/V/Co | 450 | 45 | 65 |
| P/V/Mn | 460 | 35 | 55 |
| P/V/Fe | 500 | 20 | 40 |
| P/V/La | 430 | 20 | 40 |
| P/V/Zn | 460 | 52 | 75 |
| P/V/Al | 460 | 30 | 50 |
| P/V/Ti/Cd | 430 | 30 | 50 |
| P/V/Ti/Sn | 450 | 40 | 60 |
| P/V/Ti/Zn | 430 | 51 | 75 |
| P/V/Ti/Cu | 455 | 45 | 70 |

What is claimed is:

1. A process for producing maleic anhydride which comprises oxidizing butane with molecular oxygen in the presence of a catalyst comprising an activated substrate containing phosphorus and vanadium, said substrate having a promoter post-deposited upon its surface after said substrate has been activated, said post-deposited promoter component comprising an element selected from the group consisting of magnesium, calcium, scandium, yttrium, lanthanum, cerium, uranium, chromium, manganese, iron, cobalt, nickel, copper, zinc, aluminum, gallium, indium, silicon, germanium, tin, antimony, bismuth and tellurium.

2. A process as defined in claim 1, wherein said post-deposited promoter component comprises an element selected from the group consisting of magnesium, calcium, lanthanum, cerium, chromium, manganese, iron, cobalt, nickel, zinc, aluminum, gallium, germanium, antimony, and tellurium.

3. A process as defined in claim 1, wherein said post-deposited promoter component comprises an element selected from the group consisting of magnesium, cerium, zinc, aluminum, gallium, indium, and germanium.

4. A process as defined in claim 1, wherein said post-deposited promoter component is deposited upon said solid substrate together with compounds of phosphorus or boron.

5. A process as defined in claim 1, wherein the post-deposited promoter component is zinc.

6. A process for producing maleic anhydride which comprises oxidizing butane with molecular oxygen in the presence of a catalyst comprising a substrate containing phosphorus and vanadium, said substrate having a promoter post-deposited upon its surface, said post-deposited promoter comprising an element selected from the group consisting of magnesium, calcium, scandium, yttrium, lanthanum, cerium, uranium, chromium, manganese, iron, cobalt, nickel, copper, zinc, aluminum, gallium, indium, silicon, germanium, tin, antimony, bismuth and tellurium, and said substrate further containing an integrally-incorporated promoter component.

7. A process as defined in claim 6, wherein the integrally-incorporated promoter component comprises an element selected from the group consisting of titanium, zinc, hafnium, lithium, magnesium, calcium, iron, cobalt, nickel, copper, tin, bismuth, uranium, the rare earth metals, chromium, cadmium and aluminum.

8. A process as defined in claim 6, wherein the integrally-incorporated promoter component is titanium.

9. A process as defined in claim 6, wherein the post-deposited promoter component is zinc, and the integrally-incorporated promoter component is titanium.

* * * * *

UNITED STATES PATENT AND TRADEMARK OFFICE
CERTIFICATE OF CORRECTION

PATENT NO. : 4,244,878
DATED : January 13, 1981
INVENTOR(S) : Joseph X. McDermott It is certified that error appears in the above-identified patent and that said Letters Patent are hereby corrected as shown below:

Column 2, line 66, "0.5:1" should be --1.5:1--

Column 5, line 5, insert --a-- between "as" and "chloride"

Column 5, line 52, "in" should be --to--

Column 7, line 1, "0.10" should be -- .10 --.

Column 8, line 23, "to" should be --and--

Signed and Sealed this

Sixth Day of April 1982

|SEAL|

Attest:

Attesting Officer

GERALD J. MOSSINGHOFF

Commissioner of Patents and Trademarks